(12) United States Patent
Dupoy et al.

(10) Patent No.: US 9,726,602 B2
(45) Date of Patent: Aug. 8, 2017

(54) METHOD FOR OBSERVING BIOLOGICAL SPECIES

(71) Applicants: Commissariat A L'Energie Atomique Et Aux Energies Alternatives, Paris (FR); Biomerieux, Marcy-l'Etoile (FR)

(72) Inventors: Mathieu Dupoy, Grenoble (FR); Mathieu Debourdeau, Saint Pierre d'Allevard (FR); Frédéric Pinston, Grenoble (FR)

(73) Assignees: Commissariat a L'Energie Atomique et aux Energies Alternatives, Paris (FR); Biomerieux, Marcy-L'Etoile (FR)

( * ) Notice: Subject to any disclaimer, the term of this patent is extended or adjusted under 35 U.S.C. 154(b) by 1 day.

(21) Appl. No.: 14/439,046

(22) PCT Filed: Oct. 28, 2013

(86) PCT No.: PCT/EP2013/072530
§ 371 (c)(1),
(2) Date: Apr. 28, 2015

(87) PCT Pub. No.: WO2014/067907
PCT Pub. Date: May 8, 2014

(65) Prior Publication Data
US 2015/0268163 A1     Sep. 24, 2015

(30) Foreign Application Priority Data

Oct. 29, 2012 (FR) ..................... 12 60301

(51) Int. Cl.
| | |
|---|---|
| *G01N 21/47* | (2006.01) |
| *C12M 1/22* | (2006.01) |
| *C12M 1/34* | (2006.01) |
| *C12Q 1/02* | (2006.01) |

(52) U.S. Cl.
CPC ............. *G01N 21/47* (2013.01); *C12M 23/10* (2013.01); *C12M 41/36* (2013.01); *C12Q 1/02* (2013.01); *G01N 21/4738* (2013.01); *G01N 2201/022* (2013.01); *G01N 2201/0633* (2013.01); *G01N 2201/06113* (2013.01)

(58) Field of Classification Search
None
See application file for complete search history.

(56) References Cited

U.S. PATENT DOCUMENTS

| | | | |
|---|---|---|---|
| 3,712,746 A | 1/1973 | Bergeron | |
| 6,238,879 B1 | 5/2001 | Gibbs | |
| 2008/0297795 A1* | 12/2008 | Yonggang | ............ G01B 11/026 356/326 |

FOREIGN PATENT DOCUMENTS

| | | |
|---|---|---|
| EP | 2 184 346 A2 | 5/2010 |
| FR | 2 786 498 A1 | 6/2000 |
| FR | 2 938 917 A1 | 5/2010 |
| JP | 5 184349 A2 | 7/1993 |
| JP | 2004 012398 A | 1/2004 |
| JP | 2010 051200 A | 3/2010 |

OTHER PUBLICATIONS

International Search Report and Written Opinion from International Application No. PCT/EP2013/072530 dated Dec. 18, 2013.

\* cited by examiner

*Primary Examiner* — Renee Claytor
*Assistant Examiner* — Sharon M Papciak
(74) *Attorney, Agent, or Firm* — Alston & Bird LLP

(57) ABSTRACT

A method for observing biological species on a culture medium contained in a container having at least one translucent face, the method including the steps of: a) directing a light beam onto one portion of the translucent face, so as to define at least one illuminated region and at least one non-illuminated region of the face; and b) acquiring an image of a portion of the surface of the culture medium illuminated by the light beam, the acquisition being carried out through at least one of the non-illuminated regions of the translucent face and along an optical acquisition axis forming a non-zero angle (a) with the direction of propagation of the light beam.

12 Claims, 4 Drawing Sheets

METHOD FOR OBSERVING BIOLOGICAL SPECIES

FIELD

The invention relates to a process for observing, and where appropriate detecting, biological species on a culture medium contained in a container such as a Petri dish.

BACKGROUND

Microorganisms such as bacteria are generally cultured on a culture medium (agar) contained in a Petri dish. Petri dishes are cylindrical dishes which are not very deep, consisting of a base and a lid, made of transparent material such as glass or a plastic (polystyrene). Microorganisms are generally detected by observation with the naked eye under uniform illumination; bacterial colonies generally appear in the form of more or less curved clusters of material, which can be seen through the walls or the bottom of the Petri dish. Observation through the lid is generally made difficult or impossible by the thin layer of condensation, made up of diffusing droplets having a diameter of approximately between 1 μm and 1 mm, which covers the internal surface of said lid. Thus, when the culture medium is scattering or absorbent (in the case of blood agars), it is necessary to open the Petri dish in order to observe the cultured microorganisms, but this leads to a risk of contamination.

SUMMARY

The invention aims to solve this problem. More particularly, it aims to provide a process which makes it possible to observe biological species on a culture medium contained in a container through a translucent (and therefore scattering) face thereof, it being possible for the face to be made translucent owing to a deposit of scattering material, in particular condensation, thereon.

In accordance with the invention, this objective is achieved by means of a process for observing biological species on a culture medium contained in a container having at least one translucent face, the process comprising the steps consisting in:

a) directing a light beam onto one portion of said translucent face, so as to define at least one illuminated region and at least one non-illuminated region of said face; and b) acquiring an image of a portion of the surface of said culture medium illuminated by said light beam, the acquisition being carried out through said or at least one said non-illuminated region of said translucent face and along an optical acquisition axis forming a non-zero angle with the direction of propagation of said light beam.

Advantageously, steps a) and b) can be carried out a plurality of times while defining different illuminated and non-illuminated regions of said translucent face, the process also comprising a step c) of combining the images thus acquired so as to form a "combined" image.

In particular, steps a) and b) can be carried out a plurality of times, the beam then scanning the surface of the culture medium. At each successive position of the beam, an image is acquired, said images then being processed so as to form a combined image. The combined image then constitutes a representation of the culture medium.

For example, said combined image can be obtained by combining, at each point of the surface of the culture medium, the weakest light intensity measured, that corresponds to said point, on said acquired images.

Said combined image can also be obtained by identifying a region of interest on each of the acquired images, said regions of interest then being combined so as to form the combined image.

In particular, the region of interest may comprise the projection of the light beam on the culture medium. For example, the region of interest may correspond to the projection of the light beam on the culture medium. Preferably, said region of interest does not comprise the projection of the light beam on the translucent face.

Following steps a) and b) mentioned above, it is possible to extract a zone of interest of the image, including the projection of the light beam on the culture medium. Preferably, this extracted zone of interest does not comprise the projection of the light beam on the translucent face of the container.

The process may also comprise a step d) consisting in detecting said biological species by discrimination, on said image or combined image, of light or dark regions. This detection can be carried out by an operator, or else automatically by a computer executing image processing software. This detection can be accompanied by counting the colonies, and also by their classification according to a given criterion, for example their surface area.

Advantageously, said optical acquisition axis can form an angle of at least 10°, and preferably between 30° and 60°, with said translucent face and along an optical acquisition axis forming an angle with the direction of propagation of said light beam.

Said light beam may in particular define, on said translucent face, a region illuminated in the form of a line.

According to a first embodiment of the invention, said optical acquisition axis does not coincide with the direction of specular reflection of said light beam by said culture medium, as a result of which said biological species appear as light regions on said image.

According to a second embodiment of the invention, said optical acquisition axis coincides approximately with the direction of specular reflection of said light beam by said culture medium, as a result of which said biological species appear as dark regions on said image.

Said face can be made translucent by a deposit of scattering material, in particular of droplets of condensation. More particularly, said container may be a dish, in particular a Petri dish, and said translucent face is a lid of said dish, the internal surface of which is covered with condensation.

More generally, the translucent face is placed opposite the biological species. Preferably, the translucent face is not in contact with said biological species.

BRIEF DESCRIPTION OF THE DRAWINGS

Other features, details and advantages of the invention will emerge on reading the description made with reference to the appended drawings given by way of example, in which.

DETAILED DESCRIPTION

Figure 1:
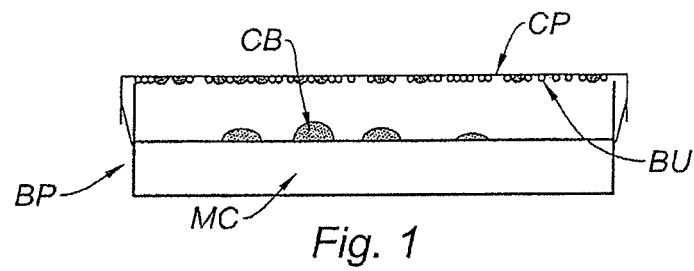
FIG. 1 shows a Petri dish exhibiting a layer of condensation on the internal surface of its lid, illustrating the problem solved by the invention.

FIG. 1 shows a sectional view of a Petri dish BP closed in an airtight manner by a lid CP, the internal surface of which is covered with a thin layer of condensation BU; although the lid CP is in itself transparent, it is made translucent by the scattering caused by the droplets of water constituting the layer of condensation. The Petri dish is partially filled with a culture medium MC of agar type, which is optionally opaque or scattering, on which bacterial colonies CB are cultured. As explained above, on the one hand, the condensation BU prevents the observation of the colonies CB through the lid, and on the other hand, removing the lid would create a risk of contamination of the culture medium or of the environment outside the Petri dish.

Figure 2A:
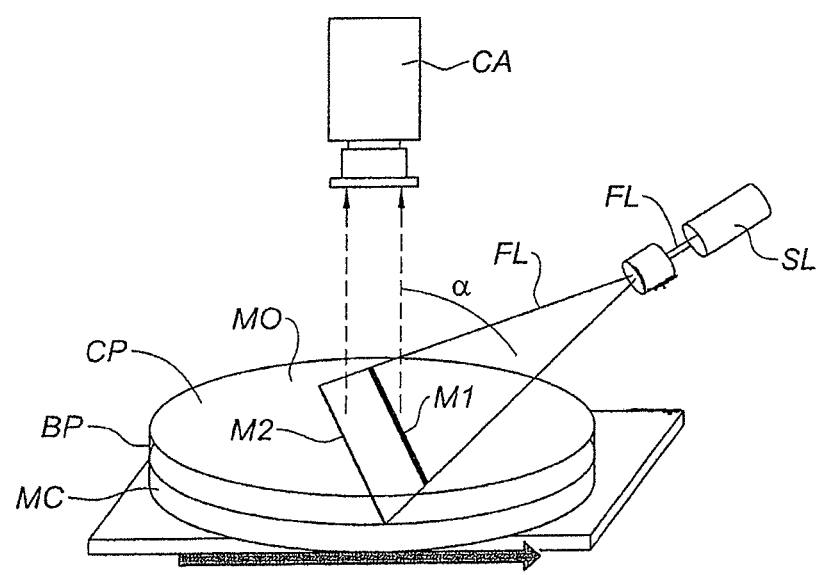
FIGS. 2A-2C represent diagrammatically the implementation of a process according to one embodiment of the invention.
Figure 2B:
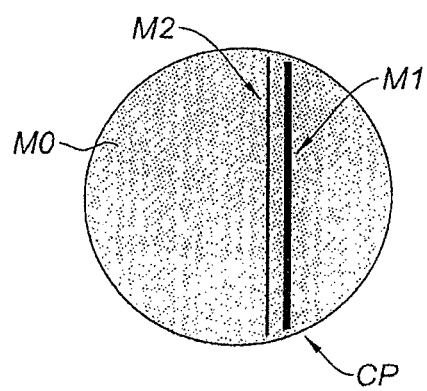

This problem can be solved, in accordance with the invention, in the manner illustrated in FIG. 2A. A light source SL (for example a laser at a wavelength of 532 nm) emits a light beam FL which is formed by an optical system. The beam formed is directed obliquely toward the lid CP, such that the intersection thereof with said lid defines an illumination pattern M1 in the shape of a line, having a length at least ten times greater than its width which is about 1 mm or less. The reference M2 indicates the pattern defined on the surface of the culture medium MC. MO indicates the part of the lid which is not illuminated (and therefore outside M1). A camera CA, directed along the normal to the surface of the lid—and therefore forming an angle $\alpha \neq 0°$ with the illuminating light beam—acquires an image of the lid CP (FIG. 2B).

Figure 2C:
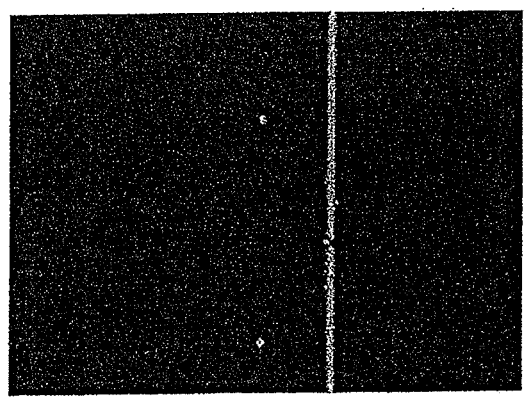

Given that the direction of propagation of the beam FL and the direction of observation of the camera (i.e. its optical axis of image acquisition) form a non-zero angle, the camera observes the illuminated region of the culture medium (pattern M2) through a non-illuminated part of the lid (MO). The bacterial colonies CB appear as bright spots superimposed on the pattern M2, owing to their scattering nature. FIG. 2C shows an image acquired by the camera CA: it is possible to note the pattern M1 in the form of a bright line, the pattern M2 in the form of a much less bright line, and two more luminous spots which correspond to bacterial colonies. Indeed:

the culture medium reflects the incident light in an essentially specular manner, but this reflection is not intercepted by the camera; only the light scattered by the irregularities of its surface, or by the condensation BU, is detected;

the bacterial colonies in fact constitute irregularities of the surface of the culture medium: for this reason, they appear more luminous;

the layer of condensation is highly scattering, which explains the brightness of the pattern M1.

The Petri dish is advantageously mounted on a translation stage, which makes it possible to scan the surface of the culture medium and to reconstitute a complete image demonstrating the bacterial colonies. The latter can then be detected by an operator or else automatically by means of an image processing process known per se, for example using thresholding, a high-pass filter or detection of contours, executed by a computer programmed in an opportune manner and connected to the camera CA.

In order to obtain the complete image, a region of interest, which corresponds to the projection of the beam on the culture medium, can be extracted on each acquired image. The width of a region of interest is preferably equal to the translation step between two successive positions of the Petri dish. Between two successively acquired images, the region of interest is shifted by a distance corresponding to the stage movement step. The regions of interest extracted during the scanning are then combined to form the complete image.

Figure 3A:
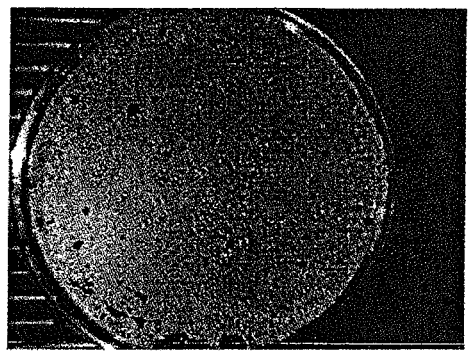
FIGS. 3A-3D illustrate the technical result of the invention, applied to the detection of bacterial colonies.
Figure 3B:
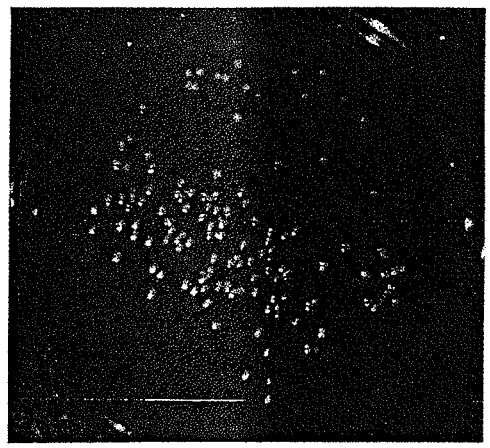
Figure 3C:
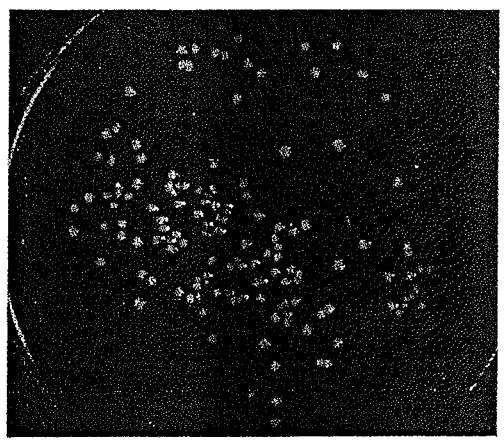
Figure 3D:
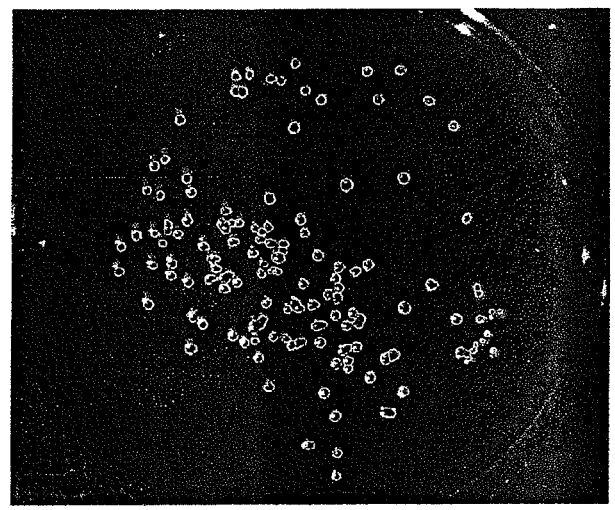

The technical effect of the invention is illustrated by FIGS. 3A to 3D, which relates to the case of a culture of *Escherichia coli* at 24 hours of culture on a blood agar (Columbia agar+5% sheep blood—Biomérieux reference 43041). The angle α is equal to 42°, the illumination being carried out by means of a Laser source, projecting a line having a width of 1 mm on the culture medium. FIG. 3A was acquired through the lid, illuminated uniformly: only the light backscattered by the condensation can be seen and the bacterial colonies are not at all distinguished. The latter are, on the other hand, clearly visible not only in FIG. 3B, acquired after having removed the lid, but also in FIG. 3C, obtained through the lid by the method described above. FIG. 3D corresponds to a superimposition of FIGS. 3B and 3C, which makes it possible to thereby verify the very good correlation thereof.

Figure 4:
FIG. 4 illustrates the technical result of the invention, applied to the detection of molds on a culture medium in a Petri dish.

The invention is not limited to the observation of bacterial colonies; by way of example, FIG. 4 shows an image obtained by means of a method as described above applied to the observation of a culture medium inoculated with a mold (*Aspergilus fumigatus*).

The invention accepts numerous variants:

It is possible for the container not to be a Petri dish, and it is possible for the observation not to be carried out through a lid having a surface covered with condensation; what counts is that a culture medium contained in a container is observed through a face of said container made translucent (scattering) by a deposit of scattering material, for example condensation or grease (finger marks), with the aim of detecting biological species.

The illumination may be carried out in monochromatic or polychromatic, or even white, light which is spatially coherent or incoherent.

Several light sources may be used: laser, lamp, light-emitting diode, beam of optical fibers, etc.

The light beam may be parallel (collimated), convergent or divergent.

The pattern M1 does not necessarily have to be in the shape of a line. However, it is essential for the light beam to define at least one illuminated region and one non-illuminated region of the lid of the Petri dish (more generally, of the translucent face of the container).

It is not essential for the beam to be directed obliquely on the lid (more generally, the translucent face) and for the direction of observation to be normal to said lid; the opposite could be true, or else both the direction of illumination and the direction of observation could be oblique. What is important is that an illuminated region of the culture medium (M2) can be observed through a non-illuminated region (MO) of the lid. For this, it is necessary for the angle α formed by the direction of illumination and the direction of observation not to be zero and preferably for it to be greater than or equal to 10°.

Figure 6A:
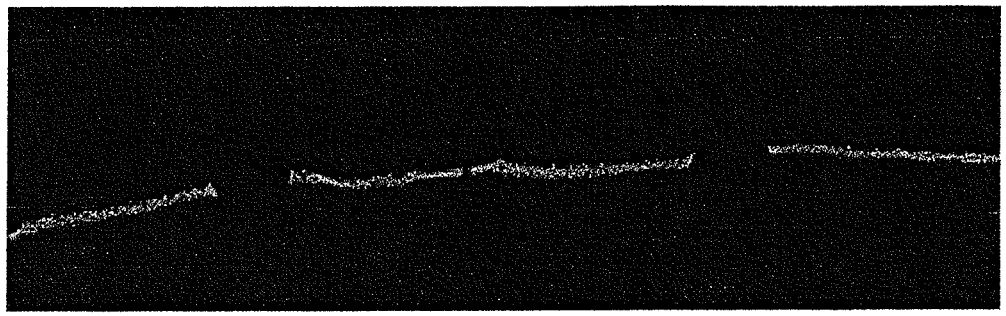
FIGS. 6A and 6B make it possible to compare an image obtained under specular reflection conditions (6A) and an image obtained outside specular reflection conditions (6B).
Figure 6B:

One particular case deserves to be pointed out. When the direction of illumination and the direction of observation form the same angle with the surface of the culture medium, i.e. are under specular reflection conditions, the pattern M2 appears bright and the biological species constitute dark spots. This situation is illustrated in FIG. 6A, where three colonies appear as interruptions of a line of illumination. FIG. 6B shows these same colonies which appear as luminous spots when the culture medium is observed outside specular reflection conditions.

Figure 5A:
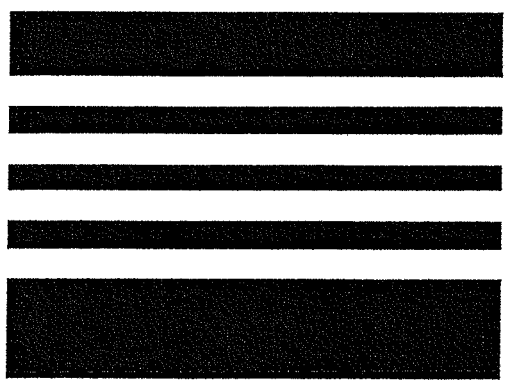
FIGS. 5A-5C illustrate the implementation of a process according to one alternative embodiment of the invention.
Figure 5C:
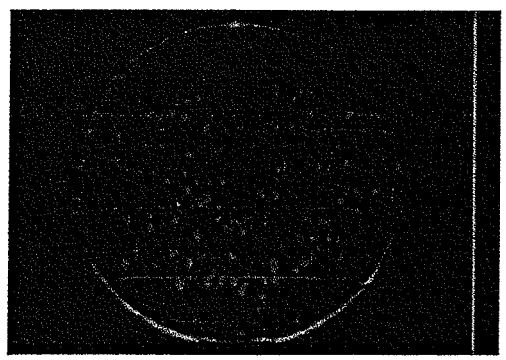
Figure 5B:
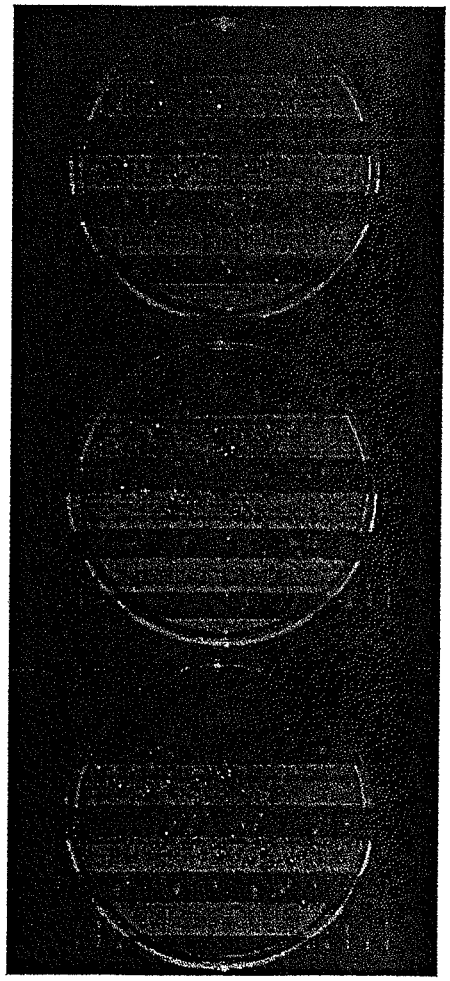

By way of example, FIGS. 5A to 5C illustrate an alternative embodiment of the invention. The illumination is carried out in white light and the pattern M1 (FIG. 5A) is in the form of four luminous bands. Three images are acquired while shifting a Petri dish relative to this pattern (which can be obtained by moving the dish, as in the case of FIG. 2A, or else the pattern), as illustrated in FIG. 5B; then the dark parts of these images are combined with one another to give a final image, reproduced in FIG. 5C. In other words, on each image, a region of interest comprising the trace of the light beam on the culture medium is extracted, the various zones of interest being combined to form the final image.

The image 5C can be constructed pixel by pixel in the following way: for each point of the lid, the weakest light intensity measured, that corresponds to said point, on the various acquired images is taken.

In other words, let $I_n(x,y)$ be the light intensity of the image number n (n=1–3 in the example of FIGS. 5A-5C) as a function of the position (x,y). Then, the combined image IC is formed by applying, at each point (x,y), the relationship: $IC(x,y)=\min_n(I_n(x,y))$. This amounts to masking the trace of the light beam FL on the translucent face of the container, which is in the form of a zone of high intensity.

The invention claimed is:

1. A process for observing biological species on a culture medium contained in a container having at least one translucent face, the process comprising the steps:
   a) directing a light beam onto one portion of said translucent face, so as to define at least one illuminated region and at least one non-illuminated region of said face; and
   b) acquiring an image of a portion of the surface of said culture medium illuminated by said light beam, the acquisition being carried out through said or at least one said non-illuminated region of said translucent face and along an optical acquisition axis forming an angle ($\alpha$) greater than or equal to 10° with the direction of propagation of said light beam.

2. The process as claimed in claim 1, wherein steps a) and b) are carried out a plurality of times by defining different illuminated and non-illuminated regions of said translucent face, the process also comprising a step c) of combining the images thus acquired so as to form a combined image.

3. The process as claimed in claim 2, wherein said combined image is obtained by combining said acquired images in such a way that, at each point (x,y) of the surface of the culture medium, the acquired image presenting the weakest light intensity measured at said point is selected.

4. The process as claimed in claim 2, wherein said combined image is obtained by defining a region of interest of each acquired image, said regions of interest then being combined so as to form the combined image.

5. The process as claimed in claim 1, also comprising a step d) consisting of detecting said biological species by discrimination, on said image or combined image, of light or dark regions.

6. The process as claimed in claim 1, wherein said light beam defines, on said translucent face, an illuminated region (M1) in the shape of a line.

7. The process as claimed in claim 1, wherein said optical acquisition axis does not coincide with the direction of specular reflection of said light beam by said culture medium, as a result of which said biological species appear as light regions on said image.

8. The process as claimed in claim 1, wherein said optical acquisition axis coincides approximately with the direction of specular reflection of said light beam by said culture medium, as a result of which said biological species appear as dark regions on said image.

9. The process as claimed in claim 1, wherein said face is made translucent by a deposit of scattering material.

10. The process as claimed in claim 9, wherein said container is a Petri dish and said translucent face is a lid of said dish, the internal surface of which is covered with condensation.

11. The process as claimed in claim 1, wherein said optical acquisition axis forms an angle between 30° and 60° with said translucent face.

12. The process as claimed in claim 1, wherein said face is made translucent by a deposit of scattering material comprised of droplets of condensation.

* * * * *